US010695290B2

(12) United States Patent
Soroudi

(10) Patent No.: US 10,695,290 B2
(45) Date of Patent: Jun. 30, 2020

(54) NON-IRRITATING, NON-BLURRING, PHOTOSTABLE OPHTHALMIC SUNSCREEN COMPOSITION

(71) Applicant: A. Ebbie Soroudi, M.D., M.S., A Professional Medical Corporation, Los Angeles, CA (US)

(72) Inventor: A. Ebbie Soroudi, Los Angeles, CA (US)

(73) Assignee: A. EBBIE SOROUDI, M.D., M.S., A PROFESSIONAL MEDICAL CORPORATION, Los Angeles, CA (US)

( * ) Notice: Subject to any disclaimer, the term of this patent is extended or adjusted under 35 U.S.C. 154(b) by 0 days.

(21) Appl. No.: 15/648,107

(22) Filed: Jul. 12, 2017

(65) Prior Publication Data

US 2017/0304193 A1    Oct. 26, 2017

Related U.S. Application Data

(63) Continuation-in-part of application No. 14/715,894, filed on May 19, 2015, now Pat. No. 10,420,963.

(60) Provisional application No. 62/000,071, filed on May 19, 2014, provisional application No. 62/361,189, filed on Jul. 12, 2016.

(51) Int. Cl.
| | |
|---|---|
| *A61K 9/00* | (2006.01) |
| *A61K 33/30* | (2006.01) |
| *A61K 31/495* | (2006.01) |
| *A61K 31/4192* | (2006.01) |
| *A61K 31/215* | (2006.01) |
| *A61Q 17/04* | (2006.01) |
| *A61K 8/37* | (2006.01) |
| *A61K 8/29* | (2006.01) |
| *A61K 8/46* | (2006.01) |
| *A61K 8/49* | (2006.01) |
| *A61K 8/365* | (2006.01) |
| *A61K 8/27* | (2006.01) |
| *A61K 8/40* | (2006.01) |
| *A61K 8/35* | (2006.01) |
| *A61K 8/19* | (2006.01) |
| *A61K 8/28* | (2006.01) |
| *A61K 8/41* | (2006.01) |
| *A61K 8/44* | (2006.01) |

(52) U.S. Cl.
CPC ............ *A61K 9/0048* (2013.01); *A61K 8/19* (2013.01); *A61K 8/27* (2013.01); *A61K 8/28* (2013.01); *A61K 8/29* (2013.01); *A61K 8/35* (2013.01); *A61K 8/365* (2013.01); *A61K 8/37* (2013.01); *A61K 8/40* (2013.01); *A61K 8/41* (2013.01); *A61K 8/445* (2013.01); *A61K 8/466* (2013.01); *A61K 8/496* (2013.01); *A61K 8/4946* (2013.01); *A61K 8/4966* (2013.01); *A61K 31/215* (2013.01); *A61K 31/4192* (2013.01); *A61K 31/495* (2013.01); *A61K 33/30* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 4,603,046 A | 7/1986 | Georgalas et al. | |
| 4,765,977 A | 8/1988 | Baron | |
| 4,788,007 A | 11/1988 | Baron | |
| 4,923,693 A | 5/1990 | Michalos | |
| 5,041,244 A | 8/1991 | Baron | |
| 5,552,135 A | 9/1996 | Cioca et al. | |
| 7,910,090 B2 | 3/2011 | Dueva-Koganov et al. | |
| 2007/0092457 A1 | 4/2007 | Librizzi et al. | |
| 2007/0092458 A1 | 4/2007 | Librizzi et al. | |
| 2007/0218021 A1 | 9/2007 | Wells | |
| 2009/0068255 A1* | 3/2009 | Yu ..................... | A61K 8/0212 424/450 |
| 2009/0087394 A1 | 4/2009 | Beasley et al. | |
| 2009/0098070 A1 | 4/2009 | Karpov et al. | |

(Continued)

FOREIGN PATENT DOCUMENTS

WO    WO-2009038710 A2    3/2009

OTHER PUBLICATIONS

"Final Office action dated Aug. 10, 2018 for U.S. Appl. No. 14/715,894."
U.S Pharmacopeial Convention: Safety Data Sheet; Product Identifier: Bemotrizinol; Catalog No. 1048572; 6 pages (2007).
PCT/US2017/041784 International Search and Written Opinion dated Sep. 8, 2017.
U.S. Appl. No. 14/715,894 Notice of Allowance dated Jun. 28, 2019.

(Continued)

*Primary Examiner* — David J Blanchard
*Assistant Examiner* — Sarah J Chickos
(74) *Attorney, Agent, or Firm* — Wilson Sonsini Goodrich & Rosati

(57) ABSTRACT

A non-irritation, non-blurring, photostable ophthalmic sunscreen composition contains at least one of the following: bemotrizinol; bisoctrizole; tris-biphenyl triazine; and/or octyl methoxycinnamate. A liquid vehicle base is then a remainder of the solution by weight. The composition is an artificial tear formulation or an ophthalmic suspension or ointment. The composition may include at least one inorganic and/or at least one organic active ingredient. The inorganic active ingredients may include, but not be limited to zinc oxide, titanium dioxide, iron oxide, zirconium oxide, and cerium oxide. The organic active ingredients may include, but not be limited to dioxybenzone, octinoxate, octisalate, homosalate, avobenzone, octocrylene, para-aminobenzoic acid, cinoxate, methyl anthranilate, octocrylene, padimate O, ensulizole, sulisobenzone, trolamine salicylate, and ecamsule.

26 Claims, No Drawings

(56) References Cited

U.S. PATENT DOCUMENTS

| | | |
|---|---|---|
| 2010/0196291 A1 | 8/2010 | Halimi et al. |
| 2010/0226867 A1 | 9/2010 | Dueva-Koganov et al. |
| 2011/0086075 A1 | 4/2011 | Halimi et al. |
| 2011/0250153 A1 | 10/2011 | Owen et al. |
| 2012/0107253 A1 | 5/2012 | Xing et al. |
| 2012/0213842 A1 | 8/2012 | Birbara et al. |
| 2013/0028853 A1 | 1/2013 | Nurse et al. |
| 2013/0266525 A1 | 10/2013 | Piconi Longo et al. |
| 2013/0331362 A1 | 12/2013 | Smith |
| 2015/0272848 A1 | 10/2015 | Holyfield |
| 2015/0328098 A1 | 11/2015 | Soroudi |
| 2015/0328148 A1 | 11/2015 | Smith |
| 2016/0008237 A1 | 1/2016 | Goldstein et al. |

OTHER PUBLICATIONS

U.S. Appl. No. 14/715,894 Office Action dated Dec. 15, 2016.
U.S. Appl. No. 14/715,894 Office Action dated Jun. 21, 2017.
U.S. Appl. No. 14/715,894 Office Action dated Jun. 3, 2019.
U.S. Appl. No. 14/715,894 Office Action dated Nov. 2, 2017.
U.S. Appl. No. 16/540,962 Notice of Allowance dated Jan. 14, 2020.
EP17828416.2 Extended European Search Report dated Dec. 18, 2019.
Hanson, K.M., et al., Photochemical degradation of the UV filter octyl methoxycinnamate in solution and in aggregates, Photochemical and photobiological sciences. May 26, 2015, vol. 14, No. 9, pp. 1607-1616.

\* cited by examiner

NON-IRRITATING, NON-BLURRING, PHOTOSTABLE OPHTHALMIC SUNSCREEN COMPOSITION

CROSS-REFERENCE TO RELATED APPLICATIONS

This continuation-in-part patent application claims priority to application Ser. No. 14/715,894 filed on May 19, 2015 which itself claimed priority to provisional application 62/000,071 filed on May 19, 2014. This continuation-in-part application also claims priority to provisional application 62/361,189 filed on Jul. 12, 2016. The entire contents of all the priority applications (non-provisional and provisional) are hereby incorporated in full by these references.

DESCRIPTION

Field of the Invention

The present invention generally relates to a sunscreen formulation designed for protecting the eyes including the conjunctiva, cornea, lens, and retina. More particularly, the present invention relates to a non-irritating sunscreen that is applied directly onto the ocular surface of the eye for protection from ultraviolet radiation.

Background of the Invention

Ultraviolet radiation is part of the electromagnetic spectrum that reaches the earth from the sun. It has wavelengths shorter than visible light, making it invisible to the naked eye. These wavelengths are classified as UVA, UVB, or UVC. UVA has the longest of the three at 320-400 nanometers. UVA is further divided into two wave ranges, UVA I, which measures 340-400 nanometers (nm, or billionths of a meter), and UVA II which extends from 320-340 nanometers. UVB ranges from 290 to 320 nm. With even shorter rays, most UVC is fortunately absorbed by the ozone layer and does not reach the earth.

Both UVA and UVB penetrate the Earth's atmosphere and play an important role in conditions such as premature skin aging, eye damage, hair damage, and certain skin cancers.

Photoconjunctivitis and Photokeratitis describe conditions where ultraviolet radiation inflames and/or damages the delicate structures of the ocular surface (the conjunctiva and the cornea, respectively). UV exposure to the eyes (either direct or indirect) can cause severe redness, dryness, irritation, tearing, photosensitivity, and pain. This pain can be so severe as to cause chemosis and sloughing of the corneal epithelium with resultant scarring and even permanent vision loss.

Long-term ophthalmic exposure to UV radiation has been associated with permanent thickening of the conjunctiva (called a pingueculum), vascular proliferation and tissue growth over the cornea (called a pterygium), conjunctival discoloration (melanosis), even cancer (e.g., conjunctival/uveal melanoma).

Long-standing UV exposure to the eyes has also been associated with damage to the internal structures of the eyes, e.g., the natural lens and the retina. Certain forms of cataracts (e.g., nuclear sclerosis), as well as macular degeneration have been linked to the damage caused by oxidative damage from UV exposure.

Accordingly, protecting the ocular structures form UV radiation may be beneficial in preventing such oxidative damage that leads to all of these very common ophthalmic conditions. Until recently, the only proposed mechanism to protect the eyes from UV radiation has been the use of glasses with UV protection, sunglasses, and tinted contact lenses.

There is a plethora of prior art suggesting the use of different physical and/or chemical sunscreen compositions for just the skin and formulations that won't damage the eye should any formulation get within the eye, but these patents and prior art did not envision and/or describe the use of such formulations for protecting the ocular structures in any way. For example, Dueva-Koganov et al. (Pub. No.: US 2010/0226867 A1) proposed a "cosmetic and/or dermatological" composition that are non-irritating to mammalian eyes. While this is a significant advantage for a dermatological composition not to burn the eyes in case of inadvertent contact, it does not describe the application of a solution that is designed for "ophthalmic" use per se.

There have been inventions that have proposed formulations specifically for the purpose of protecting the human eye from UV radiation, but such prior art has suggested formulations that are very different than what is proposed herein with potential side-effects that may render them impractical for frequent use. Such prior art has proposed compositions that would make vision extremely blurry and/or be extremely irritating to the eyes, thus making them less suitable for frequent use by the general population.

For example Michalos (U.S. Pat. No. 4,923,693) proposed the use of 0.3-0.4% hydroxypropylmethylcellulose in the form of an eyedrop or ointment applied to the eyes prior to exposure to UV radiation). This formulation, while effective against UV radiation, would affect vision tremendously and make it difficult for the user to see clearly for hours.

Baron (U.S. Pat. No. 5,041,244) described an ophthalmic liquid sunglass that is composed of dosages of chromophores in aqueous gel to block transmission of all or various spectrums of UV from the eyes. He has described the use of high molecular weight polymers which form viscous dispersions and can be used to prolong the curation of the chromophore when the gel is applied to the eye. This alone would cause significant blurring of the users' vision. Further, there is no mention of the irritation that's caused once this mixture is directly applied to the eye. This makes Baron's invention not entirely practical for frequent use by the public.

Smith (U.S. Publication Number 2013/0331362 A1) has described an Ophthalmic Solution For Absorbing Ultraviolet Radiation and Method For Absorbing Ultraviolet Radiation, where he proposed two active organic ingredients to protect the eyes from UVA and UVB radiation, respectively. This formulation, while effective in theory, would cause significant irritation to the users' eyes to the point that it would render the formulation unusable due to its severe side effects. These ingredients, used as described, would also cause severe blurring of the users's vision due to the size of the molecules proposed. This would also render the Smith formulation a poor candidate for regular use. Last, when it comes to an ophthalmic preparation, the formulation must take into effect the fact that the ingredients used must be photostable (i.e., that the UV filters don't break down or degrade once exposed to UV light). The Smith patent proposes the use of avobenzone or octisalate, two of the most unstable sunscreen agents. This would further render this formulation ineffective for its proposed use.

From another standpoint, it is very important to consider how to dissolve or disperse the proposed ingredients in a mixture, which could be utilized as an eye drop/suspension/ointment. The Smith patent publication has not described a method with which the proposed ingredients could be mixed into a vehicle that could be utilized for ophthalmic use. The present invention fulfills needs for a new form of UV radiation ophthalmic protection and provides other related advantages addressing all of the challenges aforementioned.

This present disclosure describes the composition of a sunscreen solution, suspension, emulsion, and/or an ointment that is designed to be directly applied to the eye itself to protect it from UV damage without causing significant irritation to the eye or affecting the users' vision. The present invention fulfills these needs for a new form of UV radiation protection and provides other related advantages.

SUMMARY OF THE INVENTION

Advances in our understanding of the sun protective effects of organic and inorganic ingredients has lead to the development of sunscreen preparations with very effective protection against the ultraviolet rays of the sun. Until now, the effects of these ingredients has only been described for the skin, and the prior art has warned against the use of such ingredients on the ocular surface. In fact, people are asked to rinse their eyes thoroughly in case such ingredients get into their eyes. The present invention describes the specific use of such ingredients onto the ocular surface itself. The present invention proposes formulations that provide very high SPF for the eyes, while causing minimal irritation without making vision blurry.

Examples of embodiments of the present invention include compositions that are manufactured as ophthalmic solutions, emollients, creams, or ointments that can be instilled directly on the eyes. It is understood that the use of the term "ophthalmic solution" shall include emollients, creams and ointments that can be instilled directly on the eyes.

An embodiment of the present invention of an ophthalmic sunscreen solution, comprises: a first portion comprising 0.25 percent to 15 percent by weight, wherein the first portion comprises at least one of the following: bemotrizinol; bisoctrizole; tris-biphenyl triazine; and/or octyl methoxycinnamate; and a second portion comprising a liquid vehicle base comprising a remainder of the solution by weight.

Other embodiments may include a third portion comprising an inorganic active ingredient comprising 0.25 percent to 15 percent by weight. The inorganic active ingredient may be selected from the group consisting of titanium dioxide, zinc oxide, iron oxide, zirconium oxide, cerium oxide and mixtures thereof and wherein the inorganic active ingredient is in micronized form or nanoparticle form.

Other embodiments may include a third portion comprising an organic active ingredient comprising 0.25 percent to 15 percent by weight and wherein the organic active ingredient is in micronized form or nanoparticle form. The organic active ingredient may be selected from the group consisting of dioxybenzone, octinoxate, octisalate, homosalate, avobenzone, octocrylene, para-aminobenzoic acid, cinoxate, methyl anthranilate, octocrylene, padimate O, ensulizole, sulisobenzone, trolamine salicylate and ecamsule.

The first portion may comprise 0.25 percent to 10 percent by weight. The first portion may comprise 0.25 percent to 5 percent by weight. The liquid vehicle base may be water-based or oil-based.

Other embodiments may include an emulsifier. The emulsifier may be selected from the group consisting of a silicone-based emulsifier, a polyethylene glycol emulsifier, a polysiloxane emulsifier, a glyscoside emulsifier, an acrylic-based emulsifier and combinations thereof. The emulsifier may comprise polysorbate, carbomer and/or castor oil.

Other embodiments may include an emollient. The emollient may be selected from the group consisting of aloe extracts, oleaginous esters, ethers and combinations thereof. The emollient may comprises an anhydrous lanolin and/or an oleaginous ingredient.

Other embodiments may include a preservative, wherein the preservative is an ionic-buffered preservative, a detergent or an oxidizing detergent.

Other embodiments may include a chelating agent or an antioxidant.

The ophthalmic sunscreen solution may be in the form of an eye drop, a suspension, an emulsion, or an ointment, all of which are synthesized specifically to be applied onto the ocular surface.

Other embodiments may include an ophthalmic demulcent, wherein the ophthalmic demulcent is a cellulose derivative demulcent or a liquid polyol.

Other embodiments may include a hypertonicity agent, wherein the hypertonicity agent is sodium chloride.

Other embodiments may include an ophthalmic lubricant or an ophthalmic astringent.

The first portion may be in micronized or nanoparticle form.

Another embodiment of the present invention includes an ophthalmic solution comprised of diluted forms of an inorganic active ingredient such as titanium dioxide, zinc oxide, iron oxide, zirconium oxide, cerium oxide, or mixtures thereof. This composition may also contain a weak concentration of an organic active ingredient such as avobenzone, octinoxate, octisalate, homosalate, octocrylene, para-aminobenzoic acid, cinoxate, dioxybenzone, methyl anthranilate, octocrylene, padimate O, ensulizole, sulisobenzone, trolamine salicylate, ecamsule, and mixtures thereof.

An example embodiment of the present invention includes an ophthalmic sunscreen composition which is comprised of anywhere from 0.25% to up to 15% zinc oxide by weight.

Another example of this invention includes embodiments comprised of octinoxate and/or octisalate.

Another example of this invention includes embodiments comprised of an emulsifier, silicone- or acrylic-based, glycosides, polyethylene glycols, or a mixture thereof.

Another example of this invention includes embodiments comprised of sunscreen composition comprising an emulsifier selected from the group consisting of Arlacel P 135, DC 9011 silicone elastomer, Abil WE 09, Abil EM-90, Emulgade 68/50, Simulgel A, Simulgel EG, and mixtures thereof.

Another example of this invention includes embodiments comprised of an emollient. Said emollient may be selected from the group consisting of Aloe extracts, ethers, oleaginous esters, and mixtures thereof.

Another example of this invention includes embodiments comprised of an emollient selected from the group consisting of actiphyte of aloe vera, Cetiol OE, Lexol IPL, octyl palmitate, neopentyl glycol heptanoate, neopentyl glycol diheptanoate, Trivent NP-13, CJ2—is alkyl benzoate, and mixtures thereof.

Other features and advantages of the present invention will become apparent from the following more detailed description, when taken in conjunction with the accompanying drawings, which illustrate, by way of example, the principles of the invention.

DETAILED DESCRIPTION OF THE PREFERRED EMBODIMENTS

Examples of ophthalmic sunscreen compositions of the present invention provide an SPF of up to 50 or higher. As the eyes are usually not in direct exposure to UV radiation as opposed to the skin, such high SPF ratings may not be necessary for the present invention, and as such, the concentration of the active (and inactive) ingredients may be much lower than those proposed for dermal use.

The application of much lower concentrations of these ingredients will lead to much lower incidences of ophthalmic irritation/stinging when applied, and will lessen the known side-effects of such ingredients. Further, by reducing the concentrations of these ingredients, possible absorption of these ingredients into the eye (i.e., through the Cornea) will be reduced as to prevent possible intra-ocular effects (e.g., cataract formation).

Compositions of the present invention are now described, but are not limited to these embodiments.

Ophthalmic sunscreen compositions according to the present invention may contain a liquid vehicle base, such as an artificial tear formulation, which may be water and/or oil-based, or an ophthalmic suspension or ointment and include at least one inorganic and at least one organic active ingredient.

Inorganic active ingredients may include, but not be limited to zinc oxide, titanium dioxide, iron oxide, zirconium oxide, and cerium oxide, optionally in micronized form as to prevent blurred vision when applied.

Organic active ingredients may include, but not be limited to dioxybenzone, octinoxate, octisalate, homosalate, avobenzone, octocrylene, para-aminobenzoic acid, cinoxate, methyl anthranilate, octocrylene, padimate O, ensulizole, sulisobenzone, trolamine salicylate, and ecamsule.

The inactive ingredients of the present invention shall also include emulsifier(s) and/or emollient(s). Silicone-based emulsifiers like polyethylene glycols, polysiloxanes, glycosides are excellent choices. Acrylic-based emulsifiers, and mixtures thereof may also be used safely for the present preparation. Emollients may include, but not be limited to aloe extracts, oleaginous esters, and ethers, or a combination thereof.

The composition of the present invention shall also include, but not be limited to preservatives, chelating agents, and/or antioxidants.

The following examples describe a composition of the present invention, but it is obviously not intended to limit the scope of the invention.

Example 1

An ophthalmic sunscreen solution can be synthesized by mixing 5% micronized zinc oxide and 3% octinoxate in an ophthalmic artificial tear formulation. This solution may contain carboxymethylcellulose sodium 0.1%; glycerin 0.25%; boric acid; calcium chloride dihydrate; erythritol; levocarnitine; magnesium chloride hexahydrate; potassium chloride; purified water; sodium borate decahydrate; and sodium citrate dihydrate.

Example 2

An ophthalmic sunscreen solution can be synthesized by mixing a range of 5% micronized titanium dioxide and 3% octisalate in an ophthalmic artificial tear solution.

Example 3

An ophthalmic sunscreen ointment can be synthesized by mixing a range of 5% micronized zinc oxide and 3% octinoxate in an ophthalmic ointment consisting of hypromellose, boric acid, sodium perborate, phosphonic acid, potassium chloride, purified water, and sodium chloride.

The present disclosure describes the composition of an ophthalmic sunscreen utilizing Tinosorb® (preferably Tinosorb M, IUPAC name 2,2'-methanediylbis[6-(2H-benzotriazol-2-yl)-4-(2,4,4-trimethylpentan-2-yl)phenol]) as its active ingredient. Tinosorb® is the trade name of a number of UV absorbers including the following: bemotrizinol (Tinosorb® S); bisoctrizole (Tinosorb® M); tris-biphenyl triazine (Tinosorb® A2B); and octyl methoxycinnamate (Tinosorb® OMC). Tinosorb® M is a photostable sunscreen composition that possesses multiple chemical characteristics over all other sunscreen agents currently available, that render it as an ideal candidate for use in a sunscreen formulation that is designed specifically to be directly applied to the ocular surface.

Bisoctrizole (marketed by BASF as Tinosorb® M and by MPI as Milestab 360, INCI methylene bis-benzotriazolyl tetramethylbutylphenol) is a benzotriazole-based organic compound that is added to sunscreens to absorb UV rays. Bisoctrizole is a broad-spectrum ultraviolet radiation absorber, absorbing UVB as well as UVA rays, which makes it an ideal active ingredient for an ophthalmic sunscreen composition. It also reflects and scatters UV adding to its SPF capability for this specific application. Bisoctrizole is a hybrid UV absorber, the only organic UV filter produced and microfine organic particles (<200 nm), like microfine zinc oxide and titanium dioxide. Where other organic UV absorbers need to be dissolved in either the oil or water phase, bisoctrizole dissolves poorly in both. Bisoctrizole is added to the water phase of a sunscreen as a 50% suspension, whereas mineral micropigments are usually added to the oil phase. The bisoctrizole particles are stabilized by the surfactant decyl glucoside. This allows for an ideal ophthalmic preparation that could be used in suspension form.

Bisoctrizole shows very little photodegradation and has a stabilizing effect on other UV absorbers, octyl methoxycinnamate (octinoxate) in particular. This is an extremely important factor when considering the very low concentration of the active ingredient that can be used in a formulation that is to be applied directly on the ocular surface. When formulated into a dermatologic sunscreen, bisoctrizole has minimal skin penetration. Work is still in progress by our laboratory to study its penetration into the Conjunctival or Corneal Tissues, but as an Ophthalmic Sunscreens, it should impregnate the surface layers of the Conjunctiva & Cornea so that its not washed out by blinking or the natural tears constantly irrigating the ocular surface. Bisoctrizole may penetrate the Conjunctiva and build a concentration in the episcleral connective tissue, and permeate through the Cornea and build an effective concentration in the eye's anterior chamber (aqueous humour) and serve as an effective barrier for UVA & UVB light that enters the eye, potentially preventing cataract formation and/or macular degeneration.

Unlike some other organic sunscreen actives, Tinosorb® has shown no estrogenic effects in vitro. Although there is very little systemic absorption of such agents when used on the ocular surface, it is a positive finding that this agent is safe in this regard. Tinosorb® one of the first UV filters that have been made available in micronized "nano" form, and used in this format, it will minimize significant irritation to the eye or affecting the users' vision. Further, Tinosorb® used in Particulate form (smaller than 100 nanometers) causes significantly less/no blurring for the user. From a preparation standpoint, Nanoparticle easily dispersible in oil or glycol systems, making it an ideal preparation for an ophthalmic emulsion.

Advances in our understanding of the sun protective effects of organic and inorganic ingredients has lead to the development of sunscreen preparations with very effective protection against the ultraviolet rays of the sun. Until now, the effects of these ingredients has only been described for the skin, and the prior art has warned against the use of such ingredients directly on the ocular surface. In fact, people are asked to rinse their eyes thoroughly in case such ingredients get into their eyes. The present invention describes the specific use of such ingredients, particularly Tinosorb®, onto the ocular surface itself. The present invention proposes formulations that provide UV protection for the eyes, while causing minimal irritation without making vision blurry.

Examples of embodiments of the present invention include compositions that are manufactured as ophthalmic solutions, emollients, creams, or ointments that can be instilled directly on the eyes. It is understood that the use of the term "ophthalmic solution" shall include emollients, creams and ointments that can be instilled directly on the eyes.

An embodiment of the present invention includes an ophthalmic solution comprised of diluted forms of Tinosorb® an inorganic active ingredient by itself, or mixed with a weak concentration of another organic active ingredient.

An example embodiment of the present invention includes an ophthalmic sunscreen composition, which is comprised of Tinosorb® in an artificial tear vehicle.

Another example embodiment of the present invention includes an ophthalmic sunscreen composition, which is comprised of Tinosorb® with an organic sunscreen (e.g., Avobenzone) in an artificial tear vehicle.

Another example embodiment of the present invention includes an ophthalmic sunscreen composition, which is comprised of Tinosorb® with an inorganic sunscreen (e.g., Zinc Oxide) in an artificial tear vehicle.

Another example embodiment of the present invention includes an ophthalmic sunscreen composition, which is comprised of Tinosorb® with an organic, as well as an inorganic sunscreen an artificial tear vehicle.

Another example of this invention includes said solution containing embodiments comprised of an emulsifier, silicone- or acrylic-based, glycosides, polyethylene glycols, or a mixture thereof.

Another example of this invention includes embodiments comprised of sunscreen composition comprising an emulsifier selected from the group consisting of Arlacel P 135, DC 9011 silicone elastomer, Abil WE 09, Abil EM-90, Emulgade 68/50, Simulgel A, Simulgel EG, and mixtures thereof.

Another example of this invention includes embodiments comprised of an emollient. Said emollient may be selected from the group consisting of Aloe extracts, ethers, oleaginous esters, and mixtures thereof.

Another example of this invention includes embodiments comprised of an emollient selected from the group consisting of actiphyte of aloe vera, Cetiol OE, Lexol IPL, octyl palmitate, neopentyl glycol heptanoate, neopentyl glycol diheptanoate, Trivent NP-13, CJ2—is alkyl benzoate, and mixtures thereof.

Compositions of the present invention are now described, but are not limited to these embodiments.

Ophthalmic sunscreen compositions according to the present invention may contain a liquid vehicle base, such as an artificial tear formulation, which may be water and/or oil-based, or an ophthalmic suspension or ointment and include at least one form of Tinosorb® (e.g., Tinosorb® M) by itself, or mixed with an organic- and/or an inorganic molecule with UV protecting features. Tinosorb® can be used in nano form, and refers to a number of UV absorbers: Bemotrizinol (Tinosorb® S), Bisoctrizole (Tinosorb® M), Tris-Biphenyl Triazine (Tinosorb® A2B), Octyl methoxycinnamate (Tinosorb® OMC).

Inorganic active ingredients may include, but not be limited to zinc oxide, titanium dioxide, iron oxide, zirconium oxide, and cerium oxide, optionally in micronized form as to prevent blurred vision when applied.

Organic active ingredients may include, but not be limited to dioxybenzone, octinoxate, octisalate, homosalate, avobenzone, octocrylene, para-aminobenzoic acid, cinoxate, methyl anthranilate, octocrylene, padimate O, ensulizole, sulisobenzone, trolamine salicylate, and ecamsule.

The inactive ingredients of the present invention shall also include emulsifier(s) and/or emollient(s). Silicone-based emulsifiers like polyethylene glycols, polysiloxanes, glycosides are excellent choices.

Acrylic-based emulsifiers, and mixtures thereof may also be used safely for the present preparation. Emollients may include, but not be limited to aloe extracts, oleaginous esters, and ethers, or a combination thereof.

The composition of the present invention shall also include, but not be limited to preservatives, chelating agents, and/or antioxidants.

The following examples describe a composition of the present invention, but it is obviously not intended to limit the scope of the invention.

Example 1: An ophthalmic sunscreen solution can be synthesized by mixing 5% micronized Tinosorb® M in an ophthalmic artificial tear formulation. This solution may contain carboxymethylcellulose sodium 0.1%; glycerin 0.25%; boric acid; calcium chloride dihydrate; erythritol; levocarnitine; magnesium chloride hexahydrate; potassium chloride; purified water; sodium borate decahydrate; and sodium citrate dihydrate.

Example 2: An ophthalmic sunscreen solution can be synthesized by mixing a range of 5% Tinosorb® with micronized titanium dioxide and 3% octisalate in an ophthalmic artificial tear solution. This solution may contain carboxymethylcellulose sodium 0.1%; glycerin 0.25%; boric acid; calcium chloride dihydrate; erythritol; levocarnitine; magnesium chloride hexahydrate; potassium chloride; purified water; sodium borate decahydrate; and sodium citrate dihydrate.

Example 3: An ophthalmic sunscreen ointment can be synthesized by mixing 5% micronized Tinosorb® M in an ophthalmic ointment consisting of hypromellose, boric acid, sodium perborate, phosphonic acid, potassium chloride, purified water, and sodium chloride.

Although several embodiments have been described in detail for purposes of illustration, various modifications may be made to each without departing from the scope and spirit of the invention. Accordingly, the invention is not to be limited, except as by the appended claims.

What is claimed is:

1. A method of protecting an eye from ultraviolet radiation damage comprising administering to the ocular surface of the eye an ophthalmic sunscreen solution, comprising:

0.25 percent to 15 percent by weight of at least one of the following active agents:
bemotrizinol;
bisoctrizole; and
tris-biphenyl triazine;
and a liquid vehicle base, wherein the liquid vehicle base is an ophthalmic artificial tear formulation.

2. The method of claim 1, wherein the ophthalmic sunscreen solution further comprises 0.25 percent to 15 percent by weight of an inorganic active ingredient.

3. The method of claim 2, wherein the inorganic active ingredient is selected from the group consisting of titanium dioxide, zinc oxide, iron oxide, zirconium oxide, cerium oxide and mixtures thereof and wherein the inorganic active ingredient is in micronized form or nanoparticle form.

4. The method of claim 3, wherein the ophthalmic sunscreen solution further comprises 0.25 percent to 15 percent by weight of an organic active ingredient and wherein the organic active ingredient is in micronized form or nanoparticle form.

5. The method of claim 4, wherein the organic active ingredient is selected from the group consisting of dioxybenzone, octinoxate, octisalate, homosalate, avobenzone, octocrylene, para-aminobenzoic acid, cinoxate, methyl anthranilate, octocrylene, 2-ethylhexyl 4-(dimethylamino) benzoate, ensulizole, sulisobenzone, trolamine salicylate and ecamsule.

6. The method of claim 5, wherein the ophthalmic sunscreen solution comprises 0.25 percent to 10 percent by weight of the at least one of the following active agents: bemotrizinol; bisoctrizole; and tris-biphenyl triazine.

7. The method of claim 5, wherein the ophthalmic sunscreen solution comprises 0.25 percent to 5 percent by weight of the at least one of the following active agents: bemotrizinol; bisoctrizole; and tris-biphenyl triazine.

8. The method of claim 5, wherein the liquid vehicle base is water-based or oil-based.

9. The method of claim 1, wherein the ophthalmic sunscreen solution further comprises an emulsifier.

10. The method of claim 9, wherein the emulsifier is selected from the group consisting of a silicone-based emulsifier, a polyethylene glycol emulsifier, a polysiloxane emulsifier, a glyscoside emulsifier, an acrylic-based emulsifier and combinations thereof.

11. The method of claim 9, wherein the emulsifier comprises polysorbate, carbomer and/or castor oil.

12. The method of claim 1, wherein the ophthalmic sunscreen solution further comprises an emollient.

13. The method of claim 12, wherein the emollient is selected from the group consisting of aloe extracts, oleaginous esters, ethers and combinations thereof.

14. The method of claim 12, wherein the emollient is an anhydrous lanolin and/or an oleaginous ingredient.

15. The method of claim 1, wherein the ophthalmic sunscreen solution further comprises a preservative.

16. The method of claim 15, wherein the preservative is an ionic-buffered preservative, a detergent or an oxidizing detergent.

17. The method of claim 1, wherein the ophthalmic sunscreen solution further comprises a chelating agent.

18. The method of claim 1, wherein the ophthalmic sunscreen solution further comprises an antioxidant.

19. The method of claim 1, wherein the ophthalmic sunscreen solution further comprises an ophthalmic demulcent.

20. The method of claim 19, wherein the ophthalmic demulcent is a cellulose derivative demulcent or a liquid polyol.

21. The method of claim 1, further comprising a hypertonicity agent.

22. The method of claim 21, wherein the hypertonicity agent is sodium chloride.

23. The method of claim 1, further comprising an ophthalmic lubricant.

24. The method of claim 1, further comprising an ophthalmic astringent.

25. The method of claim 1, wherein the at least one of the following active agents: bemotrizinol; bisoctrizole; and tris-biphenyl triazine is in micronized or nanoparticle form.

26. The method of claim 1, wherein the method does not cause blurred vision.

* * * * *